(12) United States Patent
Monuki et al.

(10) Patent No.: US 8,748,176 B2
(45) Date of Patent: Jun. 10, 2014

(54) GENERATION OF CHOROID PLEXUS EPITHELIAL CELLS FROM HUMAN EMBRYONIC STEM CELLS

(75) Inventors: Edwin S. Monuki, Irvine, CA (US); Momoko Watanabe, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/370,054

(22) Filed: Feb. 9, 2012

(65) Prior Publication Data

US 2012/0201789 A1 Aug. 9, 2012

Related U.S. Application Data

(60) Provisional application No. 61/441,271, filed on Feb. 9, 2011.

(51) Int. Cl.
| | |
|---|---|
| *C12N 5/071* | (2010.01) |
| *C12N 5/07* | (2010.01) |
| *C12N 5/00* | (2006.01) |
| *C12N 5/02* | (2006.01) |

(52) U.S. Cl.
USPC ............ 435/366; 435/354; 435/377; 435/384

(58) Field of Classification Search
USPC .................................. 435/354, 366, 377, 384
See application file for complete search history.

(56) References Cited

PUBLICATIONS

Cao et al. J. of Exp. Zoo., 311A: 368-376, 2009.*
Brevini et al. Theriogenology, 74: 544-550, 2010.*
Paris et al. Theriogenology, 74: 516-524, 2010.*
Encarta Online Encyclopedia (2006), "Invertebrate", p. 1, 2006.*
Verfaillie et al. Hematology (Am Soc Hematol Educ Program). 2002;:369-91.*
Schuldiner et al., 2000, PNAS, 97:11307.*
Chadwick et al., Blood, 102(3): 906-915, 2003.*
Watanabe et al., The Journal of Neuroscience 32(45): 15934-15945, 2012.*
Pardali et al., Cell, 20: 556-567, 2010.*
Ducy et al., Kidney International, 57: 2207-2214, 2000.*
Emerich DF, Skinner SJM, Borlongan CV, & Thanos CG (2005) A role of the choroid plexus in transplantation therapy. Cell Transplantation 14(10):715-725.
Serot J, BÈnÈ M, Foliguet B, & Faure G (2000) Monocyte-derived IL-10-secreting dendritic cells in choroid plexus epithelium. Journal of Neuroimmunology 105(2):115-119.
Serot J, BÈnÈ M, & Faure G (2003) Choroid plexus, aging of the brain, and Alzheimer's disease. Front Biosci 8:s515-521.
Sousa J, Cardoso I, Marques F, Saraiva M, & Palha J (2007) Transthyretin and Alzheimer's disease: Where in the brain? Neurobiology of Aging 28(5):713-718.
Weller RO (1998) Pathology of cerebrospinal fluid and interstitial fluid of the CNS: significance for Alzheimer disease, prion disorders and multiple sclerosis. Journal of Neuropathology & Experimental Neurology 57(10):885.
Schwarzman AL, et al. (1994) Transthyretin sequesters amyloid beta protein and prevents amyloid formation. Proceedings of the National Academy of Sciences of the United States of America 91(18):8368.
Schwarzman AL, et al. (2004) Amyloidogenic and anti-amyloidogenic properties of recombinant transthyretin variants. Amyloid 11(1):1-10.
Costa R, Ferreira-da-Silva F, Saraiva MJ, & Cardoso I (2008) Transthyretin protects against A-beta peptide toxicity by proteolytic cleavage of the peptide: a mechanism sensitive to the kunitz protease inhibitor. PLoS One 3(8).
Buxbaum JN, et al. (2008) Transthyretin protects Alzheimer's mice from the behavioral and biochemical effects of AÉtoxicity. Proceedings of the National Academy of Sciences 105(7):2681.
Choi S, et al. (2007) Accelerated A {beta} Deposition in APPswe/PS1 {Delta} E9 Mice with Hemizygous Deletions of TTR (Transthyretin). Journal of Neuroscience 27(26):7006.
Maurizi CP (2010) Choroid plexus portals and a deficiency of melatonin can explain the neuropathology of Alzheimer's disease. Medical hypotheses.
Silverberg GD, Mayo M, Saul T, Rubenstein E, & McGuire D (2003) Alzheimer's disease, normal-pressure hydrocephalus, and senescent changes in CSF circulatory physiology: a hypothesis. The Lancet Neurology 2(8):506-511.
Skinner S, et al. (2006) Choroid plexus transplants in the treatment of brain diseases. Xenotransplantation 13(4):284-288.
Johanson CE, Duncan JA, Stopa EG, & Baird A (2005) Enhanced prospects for drug delivery and brain targeting by the choroid plexus-CSF route. Pharmaceutical research 22(7):1011-1037.
Chauhan AN & Lewis PD (1979) A quantitative study of cell proliferation in ependyma and choroid plexus in the postnatal rat brain. Neuropathology and Applied Neurobiology 5(4):303-309.
Itokazu Y, et al. (2006) Choroid plexus ependymal cells host neural progenitor cells in the rat. Glia 53(1):32-42.
Kaplan MS (1980) Proliferation of epithelial cells in the adult primate choroid plexus. The Anatomical Record 197(4):495-502.
Currie DS, Cheng X, Hsu C, & Monuki ES (2005) Direct and indirect roles of CNS dorsal midline cells in choroid plexus epithelia formation. Development 132(15):3549.
Furuta Y, Piston D, & Hogan B (1997) Bone morphogenetic proteins (BMPs) as regulators of dorsal forebrain development. Development 124(11):2203.
Fernandes M, Gutin G, Alcorn H, McConnell SK, & Hebert JM (2007) Mutations in the BMP pathway in mice support the existence of two molecular classes of holoprosencephaly. Development 134(21):3789.
Hebert JM, Mishina Y, & McConnell SK (2002) BMP signaling is required locally to pattern the dorsal telencephalic midline. Neuron 35(6):1029-1041.
Cheng X, et al. (2006) Central roles of the roof plate in telencephalic development and holoprosencephaly. Journal of Neuroscience 26(29):7640.

(Continued)

*Primary Examiner* — Thaian N Ton
(74) *Attorney, Agent, or Firm* — Berliner & Associates

(57) ABSTRACT

Choroid plexus epithelial cells are generated in a culture medium using embryonic stem cells and adding an effective amount of bone morphogenetic protein and/or other members of the transforming growth factor beta (TGF-beta) superfamily. Generation of such choroid plexus epithelial cells are confirmed using a combination of genetic markers, antibodies, histology inspection, functional assays, and integration into the endogenous choroid plexus in mice.

11 Claims, 6 Drawing Sheets
(4 of 6 Drawing Sheet(s) Filed in Color)

References Cited

PUBLICATIONS

Hu JS, et al. (2008) Border formation in a Bmp gradient reduced to single dissociated cells. Proceedings of the National Academy of Sciences 105(9):3398.

Mangale VS, et al. (2008) Lhx2 selector activity specifies cortical identity and suppresses hippocampal organizer fate. Science 319(5861):304.

Monuki ES, Porter FD, & Walsh CA (2001) Patterning of the dorsal telencephalon and cerebral cortex by a roof plate-Lhx2 pathway. Neuron 32(4):591-604.

Eiraku M, et al. (2008) Self-organized formation of polarized cortical tissues from ESCs and its active manipulation by extrinsic signals. Cell stem cell 3(5):519-532.

Elkabetz Y, et al. (2008) Human ES cell-derived neural rosettes reveal a functionally distinct early neural stem cell stage. Genes & development 22(2):152.

Watanabe K, et al. (2005) Directed differentiation of telencephalic precursors from embryonic stem cells. Nature neuroscience 8(3):288-296.

Swetloff A, Greenwood S, Wade AM, & Ferretti P (2006) Growth of choroid plexus epithelium vesicles in vitro depends on secretory activity. Journal of cellular physiology 208(3):549-555.

Thomas T & Dziadek M (1993) Capacity to form choroid plexus-like cells in vitro is restricted to specific regions of the mouse neural ectoderm. Development 117(1):253.

Zhang SC, Wernig M, Duncan ID, Br stle O, & Thomson JA (2001) In vitro differentiation of transplantable neural precursors from human embryonic stem cells. Nature biotechnology 19(12):1129-1133.

Wilson P & Stice S (2006) Development and differentiation of neural rosettes derived from human embryonic stem cells. Stem Cell Reviews and Reports 2(1):67-77.

Gage F (2000) Mammalian neural stem cells. Science 287(5457):1433.

Gotz M & Huttner W (2005) The cell biology of neurogenesis. Nature Reviews Molecular Cell Biology 6(10):777-788.

Huang X, et al. (2009) Sonic hedgehog signaling regulates a novel epithelial progenitor domain of the hindbrain choroid plexus. Development 136(15):2535.

\* cited by examiner

GENERATION OF CHOROID PLEXUS EPITHELIAL CELLS FROM HUMAN EMBRYONIC STEM CELLS

CROSS REFERENCE TO RELATED APPLICATIONS

The present claims the benefit of U.S. Provisional Ser. No. 61/441,271 filed on Feb. 9, 2011, which is incorporated herein by reference in its entirety for all purposes.

FIELD OF THE INVENTION

The invention relates to choroid plexus epithelial cells. More particularly, it relates to a generation of choroid plexus epithelial cells from stem cells.

BACKGROUND OF THE INVENTION

Choroid plexus epithelial cells (CPECs) are a relatively understudied cell type in the nervous system with untapped clinical potential. These cells are the primary cells comprising the choroid plexus, the tissue that produces the cerebrospinal fluid (CSF) that bathes and nourishes the human brain. The CPECs also form a physical bather ("blood-CSF bather") and have important adsorptive functions that protect the brain from toxins. Atrophy and other defects in CPECs have been implicated in human neurodegenerative diseases, particularly Alzheimer's disease, and choroid plexus transplant studies have shown benefit in animal models of some of these diseases. The ability to generate large number of CPECs in culture, which is not currently possible, should therefore enable a number of novel clinical applications.

In prior animal model studies, whole choroid plexus dissected from donor rodents or pigs have been used as transplant sources. A human source for transplantable CPECs has not previously been available. In addition, unlike some other epithelia in the human body, the CPECs are not highly proliferative and do not turnover significantly, which makes expansion of CPECs from the endogenous choroid plexus in culture less feasible.

BRIEF DESCRIPTION OF DRAWINGS

The patent or file contains at least one drawing executed in color. Copies of this patent or patent publication with color drawing(s) will be provided by the Office upon request and payment of the necessary fee.

BRIEF SUMMARY OF THE INVENTION

Figure 1:
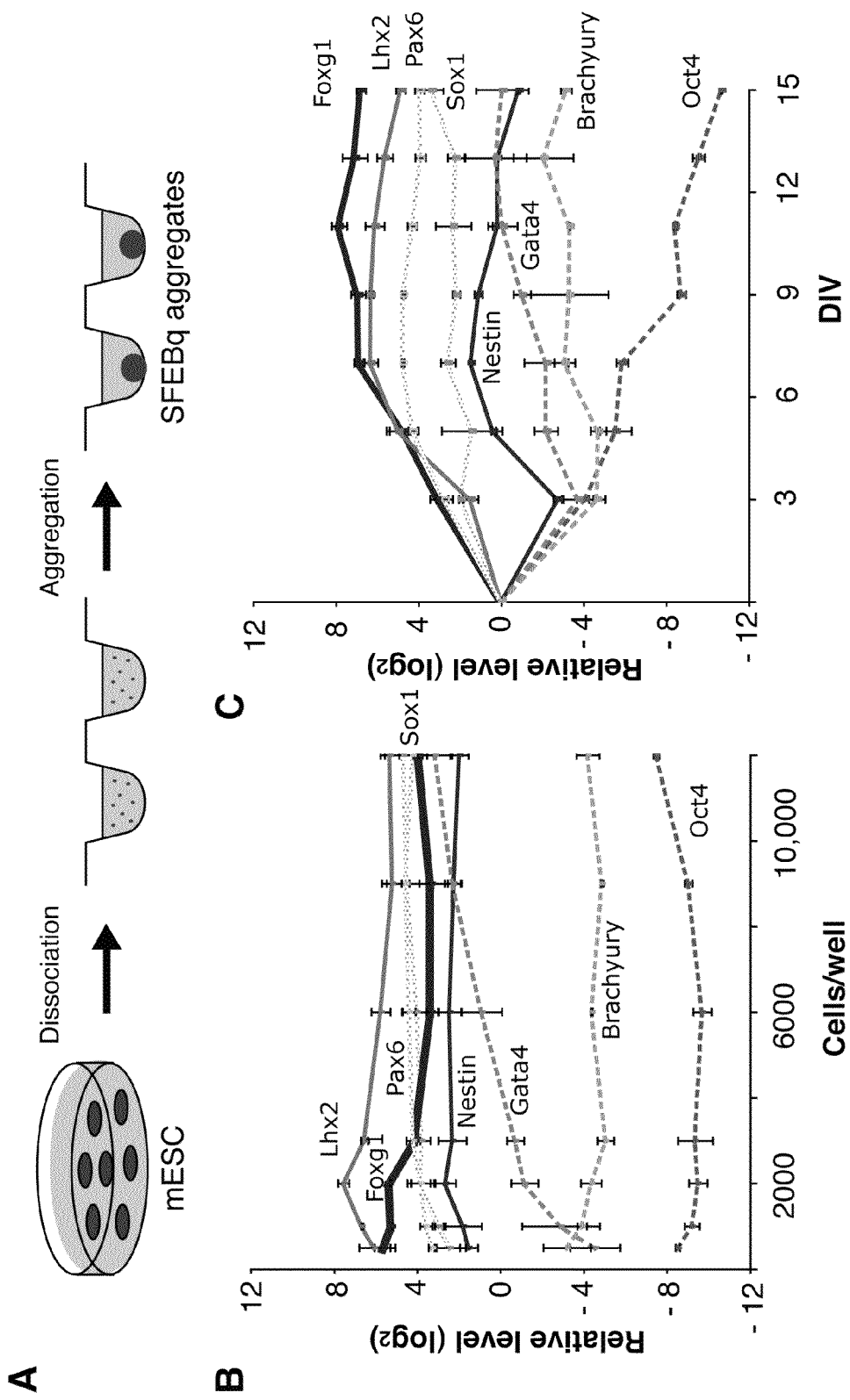
FIG. 1. Shows establishment and optimization of neuroepithelial cell (NEC) induction from mESCs. (A) Schematic of neural differentiation using the SFEBq method (29). (B) Cells/well optimization (RT-qPCR, normalized to mESCs). 2000 cells/well yielded an optimal gene expression profile for one particular #5 mESC line; the optimal range across mESC lines tested thus far (12 lines) is 2000-6000 cells/well. Error bars±SEM, n>2. (C) Temporal analysis of 2000-cell aggregates (RT-qPCR, normalized to mESCs). Plateaus for the five NEC markers were observed by 7-9 DIV. Error bars±SEM, n>2.

The method provided overcomes some of the drawbacks of the prior works because of the usage of one of the expandable stem cell lines, human embryonic stem cells (hESCs), to generate induced CPECs ("iCPEC" i.e. differentiated CPECs from any stem cell in culture which distinguish from endogenous CPECs) in large numbers in culture. Thus, the invention should enable the subsequent production of large numbers of iCPECs for a variety of downstream applications.

Such downstream applications for these iCPECs include, but are not limited to, use as therapeutics in human neurodegenerative diseases (e.g. human iCPEC transplants or replacements in patients with Alzheimer's disease), genetic engineering of iCPECs to produce large amounts of secretory proteins or peptides, and drug screens using cultured iCPECs to identify compounds that can cross the blood-CSF bather.

Provided are multiple lines of evidence for BMP sufficiency (in this case, BMP4) to induce CPEC differentiation from mouse ESC-derived neuroectodermal cells (or neuroepithelial cells, NECs), which occurs at the expense of NEC fate.

Provided are multiple lines of evidence that BMP must be added to mouse and human ESC-derived NECs—but not to later stage neural progenitor cell types (e.g. radial glia or later-stage neural stem cells)—suggesting that early-stage NECs are unique in their competency to differentiate into iCPECs. This is consistent with normal mouse and human CPEC development in vivo. Mouse radial glia and adult neural stem cells were unable to differentiate into iCPECs using the methods described herein.

Three different methods were used to generate iCPECs from mouse and human ESCs—1) an aggregation-based method (in which mouse and human ESCs were aggregated that was modified from previously established SFEBq method by Sasai's group (29), then differentiated into NECs and then iCPECs), 2) a previously-published neural rosette method (in which human ESCs plated onto a plastic surface then spread out and differentiate into neural rosettes—ref. 35—and then into iCPECs), and 3) a combined aggregate-monolayer method (in which mouse and human ESCs are differentiated into NECs in aggregates, then the aggregates are dissociated and plated as adherent monolayers prior to BMP4 addition and iCPEC differentiation).

In one embodiment, a method of inducing choroid plexus epithelial cells in vitro is provided comprising providing embryonic stem cells; and adding an effective amount of bone morphogenetic protein and/or other members of the transforming growth factor beta (TGF-beta) superfamily.

In a particular embodiment of the method of the second preceding paragraph, the stem cells are differentiated into neuroepithelial cells, and said neuroepithelial cells then differentiate into said choroid plexus epithelial cells.

In another embodiment of the third preceding paragraph, bone morphogenetic protein is added; more particularly BMP4.

In another embodiment of the fourth preceding paragraph, the embryonic stem cells are human or mouse embryonic stem cells.

In an embodiment of the fourth preceding paragraph, the neuroepithelial cells are early-stage neural progenitors, but not later-stage progenitors.

In another embodiment of the sixth preceding paragraph, the effective amount of BMP and/or other members of the transforming growth factor beta (TGF-beta) superfamily is between 0.5-50 ng/ml; more particularly 5 ng/ml.

In an embodiment, a method of engrafting endogenous CP epithelium with CPECs is provided, comprising generating said CPECs, and injecting said CPECs into the ventricle of an animal.

In a particular embodiment of the second preceding paragraph, the CPEC is either iCPEC or primary CPEC.

In an embodiment, a method to treat neurogenic disorders is provided comprising administering an effective amount of CPECs to an individual who suffers from a neurogenic disease.

In a more particularized embodiment of the second preceding paragraph, the CPEC is either iCPEC or primary CPEC; and the disease is Alzheimer's Disease.

DETAILED DESCRIPTION OF THE INVENTION

The term "BMP" as used here refers to a Bone Morphogenetic Protein, which include, but are not limited to BMP1 (GeneID: 649); BMP2 (GeneID: 650); BMP3 (GeneID: 651); BMP4 (GeneID: 652); BMP5 (GeneID: 653); BMP6 (GeneID: 654); BMP7 (GeneID: 655); BMP8 (GeneID: 656); BMP9/GDF2 (GeneID: 2658); BMP10 (GeneID: 27302); BMP11/GDF11 (GeneID: 10220); BMP12/GDF7 (GeneID: 151449); BMP13/GDF6 (GeneID: 392255); BMP14/GDF5 (GeneID: 8200); BMP15 (GeneID: 9210); GDF10/BMP3B (GeneID: 2662). These BMPs are members of the Transforming Growth Factor Beta (TGFB) superfamily. Other members of the TGFB superfamily—other than BMPs—include but are not limited to TGFBs, Growth and Differentiation Factors (GDFs), Activins, and Nodal; GDF1 (GeneID: 2657); GDF3 (GeneID: 9573); GDF8/MSTN (GeneID: 2660); GDF9 (GeneID: 2661); GDF15 (GeneID: 29455); TGFB1 (GeneID: 7040); TGFB2 (GeneID: 7042); TGFB3 (GeneID: 7043); TGFB4/LEFTY2 (GeneID: 7044); IHBA/Activin A (GeneID: 3624); IHBB/Activin AB (GeneID: 3625); IHBC/Activin C (GeneID: 3626); and NODAL (GeneID: 4838).

BMPs are dimeric molecules that are active in homodimeric or heterodimeric form. For example, the BMP4 used here is BMP4 homodimer, but BMP4/7 heterodimers are also known to exist. Accordingly, in one embodiment, it is possible to have heterodimers comprising dimers from a combination of BMP and TGFB superfamily members known to date and/or those to be discovered.

Several studies have shown that BMPs and other TGFB superfamily members share similar structures, and that certain family members can share similar functional activities (22, 28).

Although ESCs have been used, other stem cells could be utilized such as, but not limited to, induced pluripotent stem cells (iPSCs) and human parthenogenetic stem cells (hpSCs).

Others have cultured primary choroid plexus cells from a variety of organisms, but the method described herein does not require the acquisition of primary choroid plexus from humans.

The term "effective amount" as used herein refers to the amount of BMP or other TGFB molecule that is necessary to produce iCPECs, or to the amount of iCPECs that are necessary to reduce symptoms of neurodegenerative disease, as determined by a physician or the individual afflicted with said disorder.

The term treatment as used herein refers to the injections or transplantations of iCPECs, or cell mixtures that include iCPECs, into patients suffering from neurodegenerative or other diseases for which iCPECs or engineered iCPECs may serve as effective therapies.

The process provided involves the generation of human CPECs from human embryonic stem cells (ESCs) to enable such applications. In one embodiment, nervous system (neuroepithelial) cells are first generated from human ESCs using previously-published and novel protocols known to those of skill in the art. Neuroepithelial cells at relatively "primitive" stages of development are then cultured with Bone Morphogenetic Protein (BMP, specifically BMP4), which we had identified from basic studies to be an inducer of CPEC fate in mice. CPEC differentiation in culture is then assessed and confirmed using a variety of morphologic and molecular assays (histology, immunocytochemistry, RT-qPCR, electron microscopy, functional assay, and in vivo integration into endogenous choroid plexus).

Results
Efficient Neuroectodermal Induction from Mouse ESCs (mESCs)

We investigated whether NECs derived from mouse ESCs could serve as starting material for CPEC generation. To first optimize NEC induction from mESCs, we compared the Eiraku et al. ("SFEBq") (29) and Elkabetz et al. protocols (30), and also combined the two. The SFEBq method, which generates embryoid body-like mESC aggregates of consistent size (FIG. 1A), was the most efficient, reproducible, and quickest method for NEC generation based on immunocytochemistry (ICC) and RT-qPCR analyses. Accordingly, SFEBq aggregates are defined as embryoid body-like mESC aggregates generated using the SFEBq method.

Figure 2:
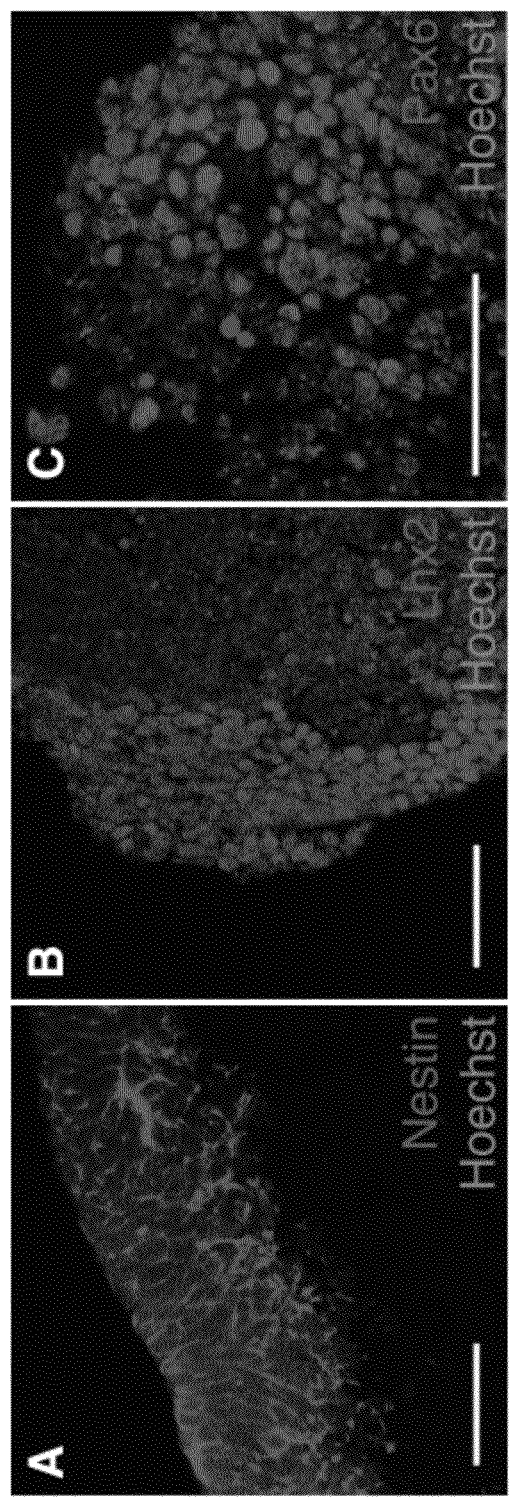
FIG. 2. (A-C) Nestin, Lhx2, and Pax6 immunostaining on 2000-cell aggregates at 7 DIV. Scale bars, 50 um.

We then optimized SFEBq-based NEC induction for cell numbers per aggregate and time in culture. 2000 cells/aggregate yielded the highest levels of generic (Nestin, Sox1) and forebrain-restricted (Foxg1, Pax6, Lhx2) NEC gene expression (FIG. 1B). Temporal RT-qPCR analysis of 2000-cell aggregates revealed plateaus for five NEC markers by 7-9 days in vitro ("DIV") (FIG. 1C). By then, aggregates often became cavitated centrally and expressed NEC antigens peripherally (FIG. 2), as described by others (29). Based on conservative counts (i.e. counting all nuclei, including in dying cavitated regions), Nestin immunopositivity approached 95%, which was comparable to previous reports (29, 31). Essentially all peripherally-located cells demonstrated Nestin positivity. Markers for ESC (Oct4), endodermal (Gata4), and mesodermal (Brachyury) fates were either significantly reduced or remained near their low baseline levels in ESCs (FIGS. 1B and C). We used the same SFEBq NEC induction method with 8 additional mESC lines and the H9 hESC line. Eight new transgenic mESC lines with a TTR::RFP CPEC reporter (line C4), ubiquitous H2B-GFP nuclear reporter (F2 and F4), both (B1-4), or neither (#5 and A3) were established. Optimal NEC induction occurred using 2000-6000 cell/well for all eight lines, with individual lines displayed consistent optima between replicates. NEC induction kinetics for #5 and C4 lines were similar, with plateaus occurring by 7-9 DIV.

Molecular, Cellular, and Ultrastructural Evidence for BMP4-Mediated CPEC Differentiation from mESC-Derived NECs BMP4 has not been applied to human NECs and no study has been reported for evidence of iCPEC from hESCs-derived NECs or from any other cell source.

Figure 3:
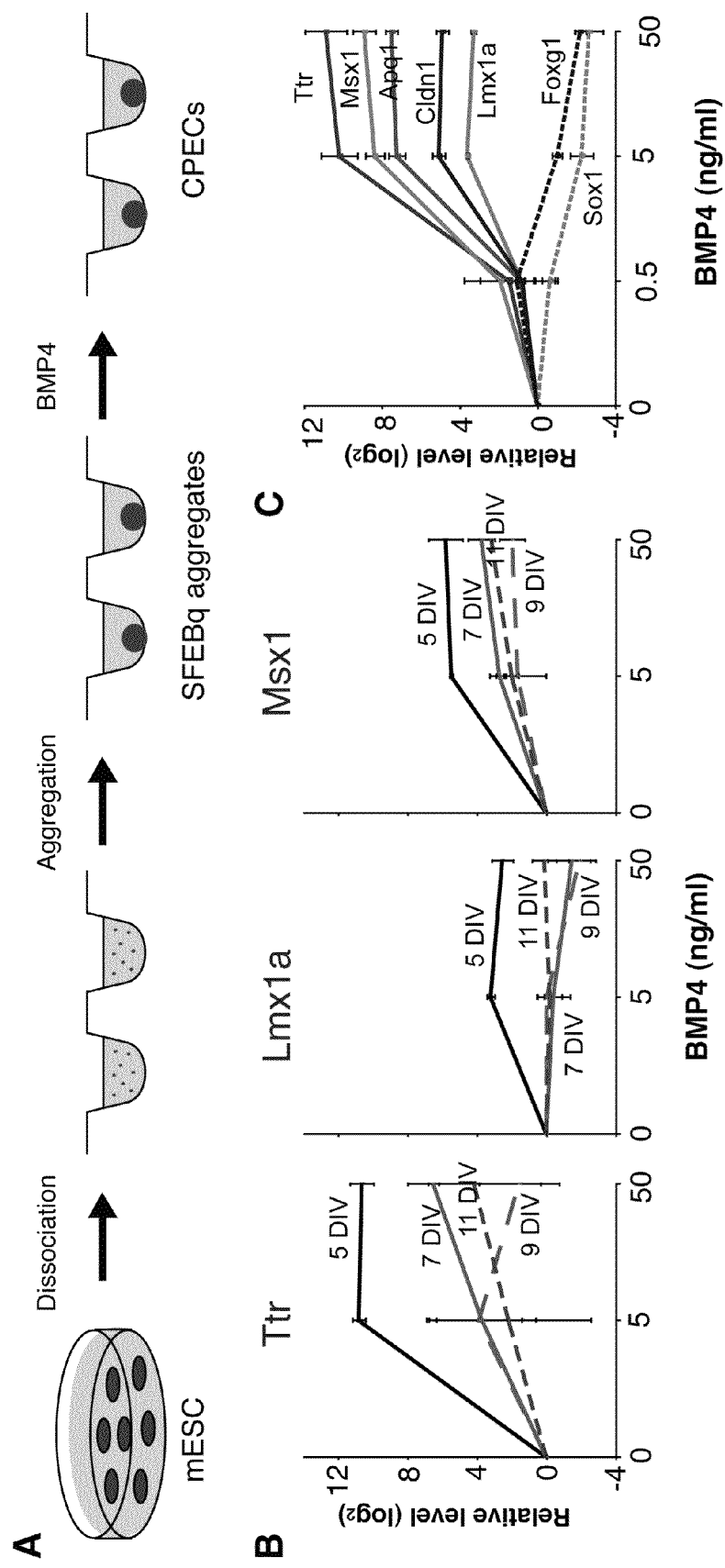
FIG. 3. CPEC differentiation from mESC-derived NECs. (A) Schematic of the CPEC differentiation method. (B) Analysis of BMP4-treated SFEBq aggregates (RT-qPCR, normalized to no BMP4 control). 5-day aggregates showed much stronger CPEC marker induction than 7-, 9-, or 11-day aggregates. Error bars±SEM, n>2. (C) CPEC marker induction, as well as downregulation of NEC markers Sox1 and Foxg1, was BMP4 dose-dependent (RT-qPCR, 5-day aggregates with BMP4 for 7 days, normalized to no BMP4 control; Error bars±SEM, n>2).

When BMP4 was given to our 5-day aggregates for 7 DIV (5 or 50 ng/ml, with full replacement every other day), the CPEC markers Ttr, Lmx1a, and Msx1 were markedly induced (FIG. 3B). Much less or no induction was seen in treated 7-, 9-, or 11-day aggregates. Two additional CPEC-specific or -restricted markers found in the Allen Brain Atlas (32)—Aqp1 and Cldn1—were also strongly induced in 5-day aggregates in a BMP4 concentration-dependent fashion (FIG. 3C). Conversely, while the radial glial markers BLBP and Glast did not decrease significantly (data not shown), the NEC markers Sox1 and Foxg1 were downregulated with increasing BMP4 concentration (FIG. 3C). Temporal analysis revealed progressive increases in CPEC marker levels between 3-7 DIV following BMP4 addition, with the highest levels seen at day 7. Significant and similar levels of CPEC gene induction were also seen with one-time BMP4 addition alone (data not shown). These findings indicate a relatively short and early critical period in culture for BMP4-mediated CPEC marker induction, which occurs at the expense of NEC markers.

Figure 4:
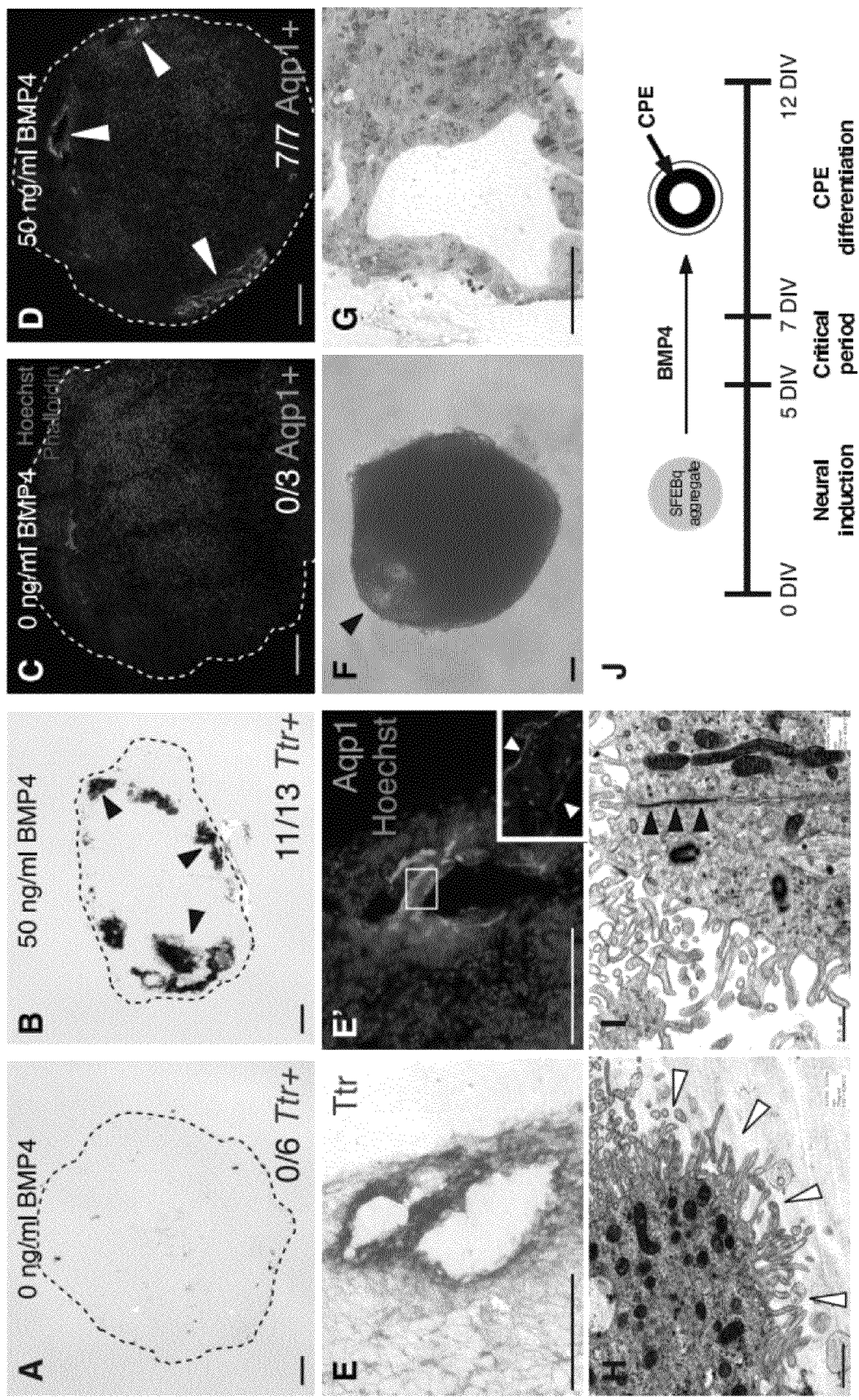
FIG. 4. (A-D) Ttr and Aqp1 expression occurred peripherally in aggregates (arrowheads) and depended on BMP4 (numbers correspond to independent aggregates scored for Ttr and Aqp1 expression). (E) Coexpression (adjacent sections) of Ttr and Aqp1, which was expressed apically (arrowheads in confocal image E'). (F-G) Peripheral vesicles within a BMP4-treated aggregate (arrowhead in F) displayed epithelial characteristics histologically (toluidine blue-stained plastic section in G). (H-I) Ultrastructure of vesicle lining cells (from the same aggregate shown in F and G) revealed extensive microvilli (white arrowheads), rare cilia, and juxtalumenal tight junctions (black arrowheads). (J) Summary of CPEC differentiation in vitro. Scale bars, A-F, 100 um; G, 50 um; H, 1 um; I, 0.5 um.

We then examined the BMP4-treated aggregates microscopically for evidence of CPEC differentiation. Cells expressing Ttr or Aqp1 were located peripherally in 50 ng/ml BMP4-treated aggregates, but not in controls (FIGS. 4A-D). At higher power, Ttr and Aqp1 expression frequently occurred in "vesicles" within peripheral regions subjacent to the surface of aggregates (FIGS. 4B,D,E,E',F,G). Lining cells in these vesicles displayed multiple light and electron microscopic characteristics of secretory and absorptive epithelial cells, including basally-located nuclei, apically-enriched mitochondria, extensive lumenal microvilli, rare cilia, and tight junctions (FIGS. 4H,I). These features—especially the microvilli, rare cilia, and tight junction findings—are characteristic of CPECs, but not other epithelia-forming neural cell types such as ependyma or retinal pigmented epithelium.

In addition to direct BMP4 applications to SFEBq aggregates, we also dissociated SFEBq aggregates into single cells after 5DIV (i.e. after they had differentiated into NECs), plated them as adherent monolayers onto PDL-laminin-coated plates at 300,000-600,000 cells, then added BMP4 (0.5-50 ng/ml BMP4) for another 5 days (10DIV total). This combined aggregation-monolayer system allows all NECs to experience the same BMP4 concentration in culture. In this system, all CPEC markers mentioned above were upregulated in a BMP4-dose dependent manner by RT-qPCR and immunocytochemistry at the expense of NEC markers. However, 5 ng/ml BMP4 was optimal, while 50 ng/ml BMP4 resulted in down-regulation of CPEC markers by RT-qPCR. The optimal concentration of BMP4 is probably between 0.5 ng/ml-50 ng/ml BMP4 in this system.

In another embodiment, the concentration of BMP (whether homodimeric or heterodimeric forms) that can be added to NECs can be between 0.5 to 50 ng/ml; more preferably, $\geq 0.5$ to $<50$ ng/ml.

Functional Evidence for Mouse CPEC Differentiation

Figure 5:
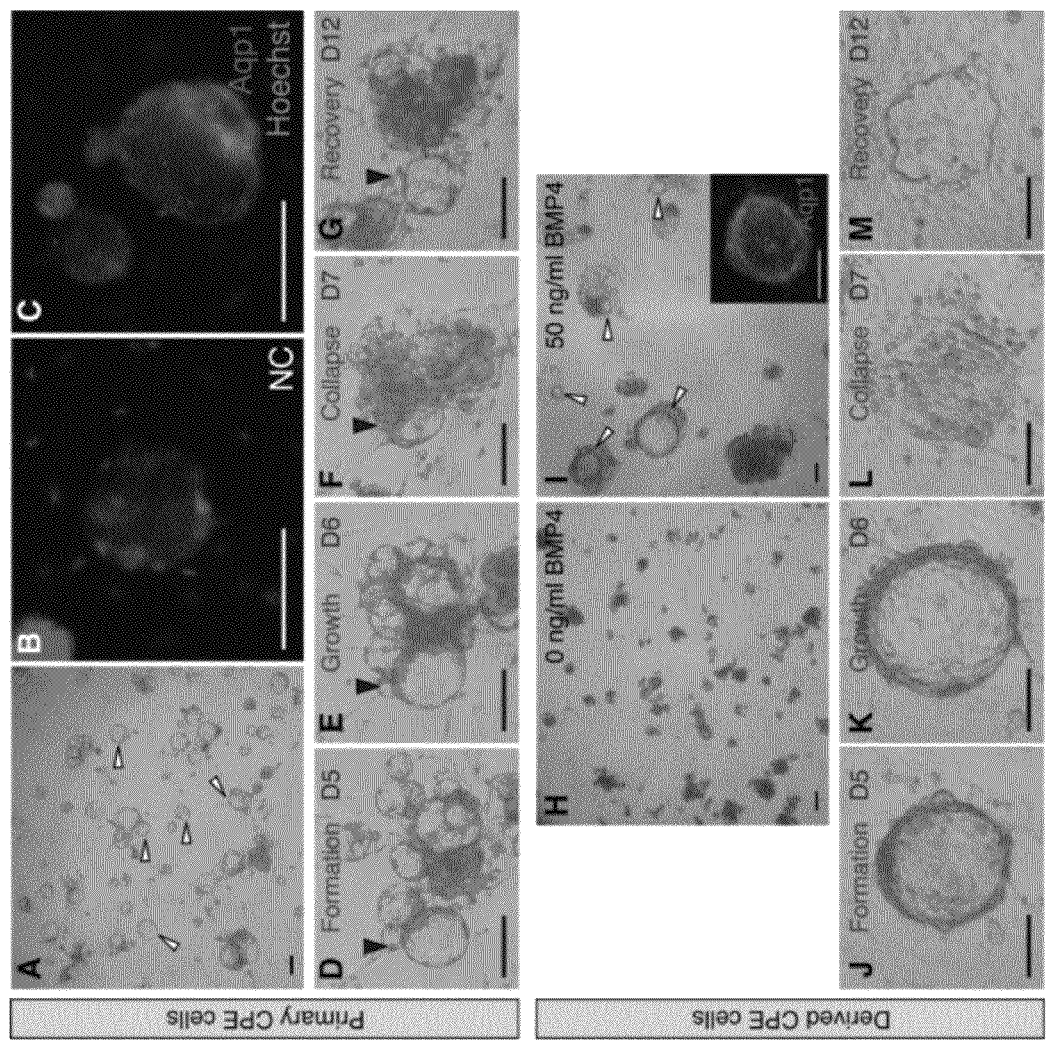
FIG. 5. Functional evidence for CPEC differentiation from mESC-derived NECs (phase contrast microscopy and immunocytochemistry). (A-C) Primary CPEC vesicles on Matrigel (arrowheads) were Aqp1-positive. (D-G) Primary CPEC vesicles enlarged (E), collapsed upon treatment with the secretory inhibitors acetazolamide and ouabain (F), then regrew upon inhibitor withdrawal (33) (G). (H-I) mESC-derived SFEBq aggregates treated with 50 ng/ml BMP4 (n=6/6), but not controls (n=0/6), formed vesicles on Matrigel that were Aqp1-positive. (J-M) mESC-derived vesicles expanded, collapsed in the presence of secretory inhibitors, then recovered after inhibitor withdrawal, in a fashion indistinguishable for primary CPECs. Scale bars, 100 um.

To assess functional activity, we adopted a well-established in vitro assay for CPEC vesicle formation and secretion (33, 34). As described previously using this assay, primary dissociated CPECs on Matrigel self-assembled into hollow vesicles that grew in diameter, collapsed after treatment with the secretion inhibitors acetazolamide and ouabain, and regrew upon inhibitor withdrawal (FIG. 5A-G). Indistinguishable vesicles formed from dissociated SFEBq aggregates treated with BMP4 (n=6/6 independent cultures), but not from controls (n=0/6; FIGS. 5H,I). Like the primary CPEC vesicles, the SFEBq-derived vesicles were Aqp1 positive (FIG. 5I, inset), grew (FIGS. 5J,K), collapsed after exposure to the secretion inhibitors (FIG. 5L), and recovered after inhibitor removal (FIG. 5M). Collectively, these studies demonstrate BMP4-mediated CPEC differentiation from mESCs at the molecular, cytological, ultrastructural, and functional levels.

Integration of iCPECs into Mouse Choroid Plexus In Vivo.

Intracerebroventricular (i.c.v.) injection coordinates for the rostral atrium of the lateral ventricle (LV) were optimized by visualizing wet-mount vibratome slices following injection of Orange CMTMR/fast green mixes (optimal: Bregma −0.1 mm AP, −1.0 mm ML, −2.5 mm DV). Injections of CPECs were then performed. Two days after injecting Vybrant CFDA-SE dye-labelled primary mouse CP cells from LV and 4V at P0-7 (usually P3-4; 400-800K cells in 4-10 ul HBSS; strain-matched CD1 CP cells into CD1 hosts), serial section analysis revealed a selective adhesion of injected cells to endogenous CP. Most dye-labelled cells were associated with ipsilateral choroid plexus, with decreasing amounts seen in 3V, contralateral LV, and 4V ChP. This distribution is consistent with the known path of CSF flow. Most interestingly, robust integration into endogenous choroid plexus was evident from confocal microscopy. Similarly robust adherence and integration into endogenous CPE was seen with primary H2B-GFP CP cells (congenic CD1 cells into CD1 host; 100K cells) after 2 or 7 days post-transplant.

Injections were then carried out on mESC-derived iCPECs. Following the injection of dye-labelled, AraC-enriched, BMP4-treated cells (#5 line, 5DIV NEC induction, 5DIV CPe differentiation with 5 ng/ml BMP4, dissociation and monolayer plating, 7DIV with 20 uM AraC, then 7DIV without AraC; 4500-5000 cells/injection; B6/CD1 cells into CD1 host), serial section analysis revealed selective adherence to and integration into endogenous ipsilateral LV CPE (82.2+/−3.3% associated with CP, 55.5+/−10.3% integrated; n=4 animals). Cells not treated with BMP4 (15K cells/injection) revealed far less integration into endogenous CPE (75.7+/−3.9% associated with CP, 6.8+/−5.0% of these integrated; n=4 animals). Very few cells were seen following a large injection of BMP4-treated cells not enriched with AraC (120K cells; n=1 animal), suggesting the importance of iCPEC enrichment. In addition, within dye-labeled clusters, peripheral cells had less dye than central cells, suggesting gap junction coupling between host and donor cells. These findings are particularly noteworthy for two reasons. First, they provide in vivo evidence for the cellular identity of iCPECs. Second, they indicate that engraftment or replacement of endogenous choroid plexus is feasible, and may be relatively straightforward, since the primary and induced CPECs appear to be naturally inclined to integrate.

In addition to injecting iCPECs/primary CPECs into the ventricles, iCPECs/primary CPECs could be injected directly into brain parenchyma or into the epidural space in the lumbar spinal cord region (i.e. the region normally accessed during routine lumbar puncture). In either of these latter cases, the iCPEC/primary CPECs may be injected with or without encapsulation (to prevent immune rejection) or could be combined with other non-epithelial cells to generate whole vascularized choroid plexus tissues that could be implanted.

Evidence for CPEC Induction from Human ESC-Derived Neural Rosettes

Figure 6:
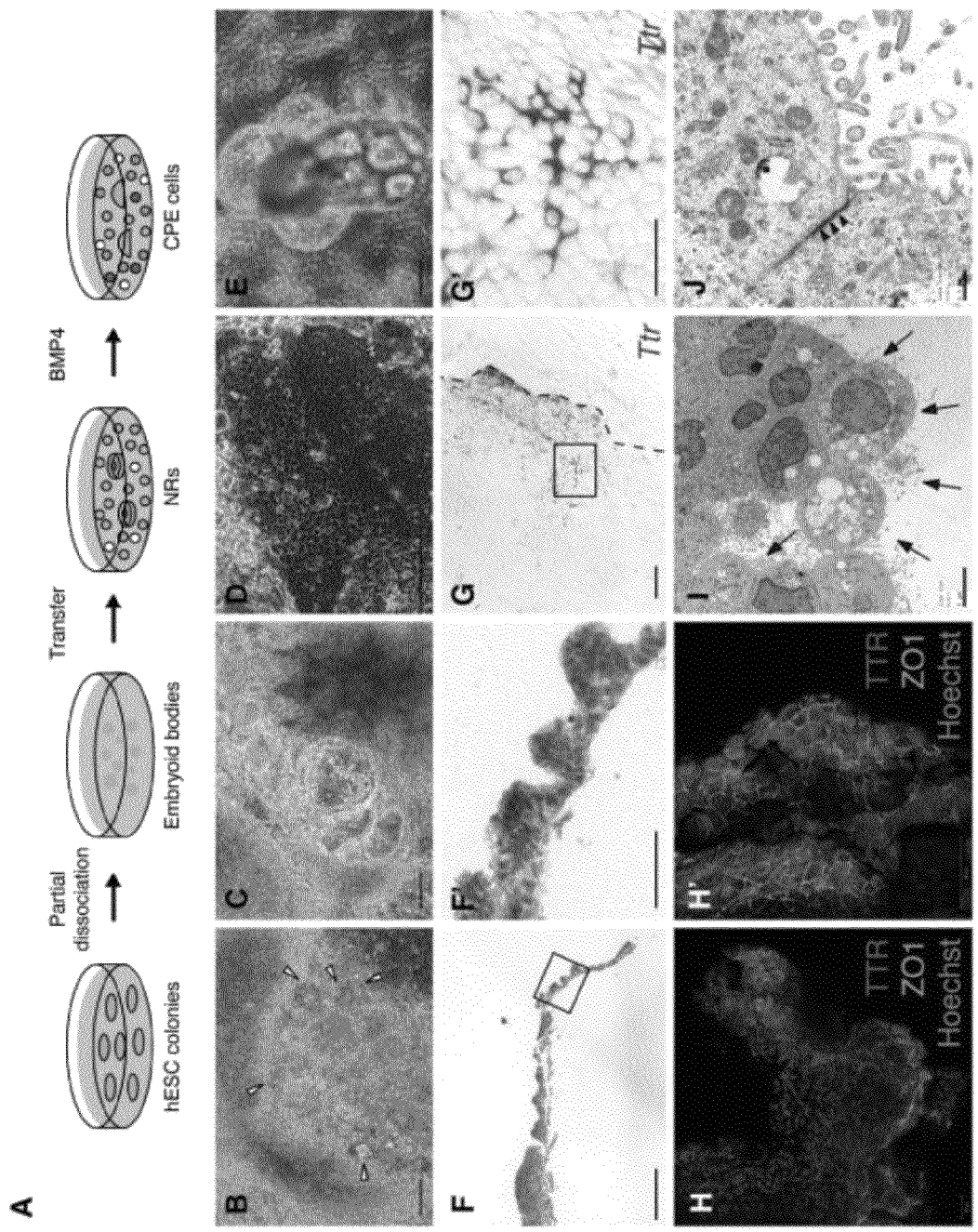
FIG. 6. CPEC differentiation from hESC-derived NECs. (A) Schematic of the CPEC differentiation method; NR, neural rosettes. BMP4 was applied for 20 days to NR-containing cultures (35) beginning at 16 DIV. (B-E) H1-derived NRs transformed directly into vesicular structures (same field shown in B and C), which eventually "collapsed" to form flat epithelial sheets (D). Occasional multivesicular bodies also formed (E). (F) H&E-stained section of an H1-derived colony at 36 DIV. The peripheral region of the colony where NRs initially formed adopted an epithelial, papillary morphology reminiscent of CPEC (inset enlarged in F'). (G) Ttr expression at the periphery of an H9-derived colony (inset enlarged in G'). (H-H') Extensive colocalization of TTR and ZO1 at the periphery of an H1-derived colony (H and H' from different regions of the same colony). (I-J), Ultrastructure of H1-derived vesicle-lining cells demonstrating extensive lumenal microvilli (arrows), rare cilia, and juxtalumenal tight junctions (arrowheads). Scale bars, B-G, 100 um: F', G', H, and H', 50 um: I, 5 um: J, 0.5 um.

We then attempted to derive iCPECs from human ESCs using an analogous approach. To first generate NECs, we used the Zhang et al. method (35) to generate neural rosettes (NRs) (FIGS. 6A,B) with predominant forebrain character (30). Strikingly, upon BMP4 addition (0.5-15 ng/ml), H1-derived NRs transformed directly into expanding vesicular structures (FIGS. 6B,C), which were evident by 7 DIV after BMP4 addition and were reminiscent of the mNEC-derived CPEC vesicles. Eventually, the hESC-derived vesicles transformed into flat epithelial sheets (FIG. 6D), and occasional multivesicular bodies also formed (FIG. 6E). Similar morphologic transformations, albeit to a lesser degree, were seen in control H1 cultures without exogenous BMP4, but these cultures also expressed high levels of endogenous BMPs (36) (data not shown). H9 cultures yielded similar morphologic changes, although NR-to-vesicle transformations were less prominent. Cross-sections of H1-derived vesicular regions revealed a papillary morphology reminiscent of endogenous CPE (FIGS. 6F,F'), and H1-derived vesicular and H9-derived monolayer regions exhibited prominent TTR and ZO1 co-expression (FIGS. 6G-H'). Ultrastructurally, abundant cells from H1-derived vesicular regions exhibited features of normal CPECs, including extensive lumenal microvilli, rare cilia, and juxtalumenal tight junctions (FIGS. 6I,J). These findings demonstrate CPEC differentiation from hESC-derived NECs, which can occur directly from NRs.

We also generated human CPECs by applying the SFEBq neural induction method to human ESCs (H9 line). H9 hESCs were optimized for aggregate size and assessed for NEC gene expression over time. 9000-cell SFEBq aggregates were optimal, and NEC expression plateaued by 18-24 DIV. BMP4 (0-15 ng/ml) was applied to 12-, 15-, 18-, 21-, and 24-DIV aggregates. CPEC markers Ttr, Otx2, and Lmx1a were upregulated with 18 to 24-DIV aggregates and 21-DIV aggregates showed the best responsiveness to BMP4. In the absence, significant upregulation of CPEC markers were not detected, suggesting that iCPEC fate was BMP4 dependent, as it was in the mESC-based system. Based on RT-qPCR studies, peak expression of NEC markers, but not radial glial markers, coincided with the 21 DIV aggregates. This suggested that, as in the mESC-based system, peak competency for iCPEC induction in the hESC-based system coincides with NEC fate.

In another embodiment of the invention, other BMPs or TGFB superfamily members—such as BMP2 homodimer, BMP2/7 heterodimer, BMP4/7 heterodimer, or TGFB 1—could be used to generate iCPECs from human pluripotent stem cells.

Discussion

Our data provide multiple levels of evidence for CPEC differentiation from mouse and human ESC-derived NECs. The molecular and ultrastructural findings, together with the evidence for NEC origin and vesicle formation, exclude other mouse and human non-CPEC fates as possibilities. Within the nervous system, prominent Ttr expression is nearly exclusive to CPECs (6, 8), and the cells of interest have a clear neural origin—the mouse and human cells arise from SFEBq aggregates that are nearly 100% Nestin positive, and the human cells differentiate directly from NRs. The CPEC marker panels alone also exclude most other non-neural possibilities. Among the few epithelial cell types of neural origin known (or with theoretical potential) to form vesicles in culture, ependymal cells lack Ttr and have abundant cilia rather than microvilli, and retinal pigmented epithelial cells contain distinctive melanosomes, which were absent. In addition, iCPECs were selectively able to integrate into endogenous CPE after intraventricular injections, further supporting their CPEC identity and providing proof-of-concept for CPEC replacement via intraventricular injection.

The dependence of CPEC induction on BMP4 in the mouse and human ESC studies provides evidence for BMP4 sufficiency to induce CPEC fate. This complements previous findings of BMP4 sufficiency to partially rescue CPEC fate in roof plate-ablated explants (25) and to ectopically induce CPEC fate in normal explants (unpublished observations).

Our evidence for mouse and human CPEC differentiation from NECs also adds to the repertoire of known NEC fates in culture. "Neural stem cells" (NSCs) of the CNS include NECs and radial glia in embryos and fetuses, and adult NSCs of the hippocampus and subventricular zone. Although the potential of these NSCs in vivo can be more limited, all of these NSC types can self-renew and differentiate into neurons, astrocytes, and oligodendrocytes in culture (37, 38). Our studies therefore add a fourth distinctive cell type (CPECs) to this list. The relatively short and early critical period for mouse CPEC induction in vitro, which coincides with peak NEC fate, mirrors the critical period defined in vivo for mouse forebrain CPEC specification (embryonic day 8.5-9.5) (34). Together, these findings suggests that the CPEC-competent NSC is the NEC rather than radial glia (39). This further implies that the NEC represents the only true "neural" stem cell (i.e. a stem cell capable of generating all neural derivatives) among cell types currently regarded as NSCs.

In one embodiment, aggregated stem cells can be grown and differentiated into aggregated NECs; whereupon these aggregated NECs can unexpectedly then be grown into iCPECs. In another embodiment, these aggregated NECs can first be dissociated and then differentiated into iCPECs.

Materials and Methods

Histochemistry, Immunostaining, In Situ Hybridization, and Electron Microscopy.

These methods were performed as described (21, 25-27). Toluidine blue stains and electron microscopy were performed by the UCI Pathology Services Core. SFEBq aggregates were processed as for embryonic mouse brain tissue. For nuclear antigens, aggregates were occasionally fixed in 4% paraformaldehyde (PFA)/0.1% saponin/0.1M sucrose. Human cell ISH on coverslips was carried out as described (21, 25-27) without dehydration steps. Antibodies used: Aqp1 (Millipore AB2219, 1:500), BrdU (Millipore MAB3510, 1:1000), Nestin (DHSB Rat-401, 1:500), Lhx2 (27) (1:100), Pax6 (DSHB, 1:2000), ZO1 (Invitrogen 61-7300, 1:100), Sox2 (Santa Cruz Biotechnology sc17320, 1:100), TTR (Abcam ab9015, 1:500), Alexa 488 and 555-conjugated secondary antibodies (Molecular Probes, 1:100). Additional reagents: Hoechst 33342 (Molecular Probes), Phalloidin-TRITC (Sigma, 1:1000, added to secondary antibody solution), Ttr ISH template (IMAGE clone 1078224).

RT-qPCR Analyses.

These were performed as described (21, 26) on a StepOne Plus (Applied Biosystems, Carlsbad, Calif.) using 18S normalization and Excel for graphing and statistics (two-tailed t-tests assuming equal variance). All primers and amplicons were validated as described (21, 26). All studies represent n>2 biological replicates per condition, unless otherwise specified.

Imaging.

Epifluorescence and brightfield imaging were performed as described (26, 27). Selected images were acquired using a Zeiss LSM710 confocal microscope and Zen LE software. Aqp1-stained vesicles were imaged on a Nikon Eclipse Ti (optics for imaging through plastic) and captured using Nikon NIS-Elements AR3.00 software. Phase-contrast images were taken on a NikonTS100 or EVOS microscope (Advanced Microscopy Group, Bothell, Wash.). All images were processed, complied, and adjusted in Adobe Photoshop as described (26, 27).

Cell Counts.

Nestin, Lhx2, and Pax6 images (FIG. 2) were manually counted in Photoshop from two biological replicates and two different confocal planes per replicate. Denominators for Nestin studies included all Hoechst-stained cells, including those in central cavitating regions of SFEBq aggregates; Lhx2 and Pax6 counts were restricted to the periphery of aggregates. Positivity figures: Nestin 96.9±SEM 3.13% (n=4890 cells), Lhx2 36.8±1.58% (n=4036 cells on the periphery), Pax6 50.8±5.12% (n=5387 cells on the periphery).

Mouse ESC Culture.

New mouse ESC lines were derived by Robin Wesselschmidt (Primogenix, Inc.) from blastocysts derived from either R26CreER/CreER;Lhx2cKO/cKO×R26+/+; Lhx2cKO/cKO or R26CreER/CreER;Lhx2+/+×R26+/+; Lhx2+/+ matings (C57BL/6 with minor CD-1 background) (27) or by the UCI Transgenic Mouse Facility (TMF). Lines were subsequently expanded by the UCI TMF or in the Monuki lab. The #5 line used for most of these studies (R26CreER/+Lhx2cKO/cKO without Lhx2 inactivation) was confirmed for markers of pluripotency (Oct4, Sox2, and alkaline phosphatase staining, all nearly 100%). The C4 line (TTR::RFP-positive) was also used in more recent studies. Mouse ESCs were cultured on mitomycin C-treated MEFs (Millipore) on 0.1% gelatin-coated plates for at least two passages after thawing prior to initiating experiments. Media used was Low Osmo DMEM (Hyclone, Waltham, Mass.) with 15% ESC-qualified Fetal Bovine Serume (Hyclone), 5% Serum Replacement (Hyclone), 2 mM L-glutamine (Invitrogen), 1,000 U/ml LIF (Millipore), 0.1 mM beta-mercaptoethanol (Sigma), and Penicillin-Streptomycin (Invitrogen). Mouse ESCs were maintained at 5% CO2 with daily media changes and every other day splits. Experiments were conducted on cells between passage numbers 11 and 40. All studies represent n>2 biological replicates per condition, unless otherwise specified.

Mouse NEC and CPEC Differentiation.

Neural differentiation was adapted from Eiraku et al. (29). Briefly, mESCs were passaged for two hours onto gelatin-coated plates to reduce MEF load, dissociated to single cells using trypsin, then plated at varying concentrations onto ultra-low attachment U-bottom 96-well plates (Corning #7007, Lowell, Mass.) to form SFEBq aggregates. Differentiation media (29) was replaced initially, then every other day, with fresh media containing 0.5 to 50 ng/ml BMP4 (R&D Systems). Neural rosette (NR) cultures were based on the Elkabetz et al. method (30). Compared to the SFEBq method, this NR method was longer (11 DIV total), generated more variably-sized aggregates as intermediates, showed lower neural induction efficiency (~50% Nestin positivity), and was less consistent overall in our hands. For the combined SFEBq/NR method, we first generated SFEBq aggregates for 5 DIV, then transferred aggregates into adherent mNR conditions for another 2 DIV (7 DIV total). This resulted in consistent and efficient neural induction, including NRs (~95% Nestin positivity), but was not better than the SFEBq method alone and involved more manipulation.

CPEC Vesicle Culture.

Primary CP cells or SFEBq-derived cells were cultured on Matrigel as previously described (33, 34). Briefly, Matrigel (BD Biosciences, San Jose, Calif.) was mixed 1:1 with DMEM (Invitrogen) and incubated for at least 30 min at 37 C. BMP4-treated SFEBq aggregates at 12 DIV were dissociated with TrypLE Express (Invitrogen) and plated at 500,000 to 600,000 cells/well onto Matrigel-coated 6-well plates in DMEM with 10% FBS, 2 mM L-glutamine, NEAA, and sodium pyruvate (Invitrogen). After vesicles formed, selected cultures were treated with 100 uM acetazolamide (Sigma) and 5 mM ouabain (Sigma) for 24 hrs, followed by washout 2-3× with fresh media. Vesicles were photographed 4-5 days after drug removal. Time for recovery was similar to previous descriptions using primary CPECs (33).

Human ESC Culture.

Human ESCs (H1 and H9 lines; WiCell Research Institute, Madison, Wis.) were cultured on 0.1% gelatin-coated plates with mitomycin C-heated MEFs (Millipore). Media was KO DMEM/F12 (Invitrogen) with 20% Knockout Serum Replacement (Invitrogen), 2 mM GlutaMax (Invitrogen), 4 ng/ml FGF2 (Invitrogen), 0.055 mM beta-mercaptoethanol (Invitrogen), and non-essential amino acids (Invitrogen). Human ESCs were maintained at 5% CO2 with daily media changes. Cells were passaged approximately weekly. Experiments were performed on cells between passages 50-70.

Three Methods of Human NEC and CPEC Differentiation.

1) Neural rosette (NR) method. Neural induction with NR formation was adapted from Zhang et al. (35). Human ESC colonies were partially dissociated with 1 mg/ml dispase, then plated in suspension to form embryoid bodies (EBs) for 3 DIV. EBs were then transferred to suspension culture with neural induction media—DMEM/F12 (Invitrogen), N2 (Invitrogen), NEAA, heparin (2 ug/ml) and FGF2 (20 ng/ml)— for another two days. On 6 DIV, EBs were transferred to adherent PDL/laminin-coated plates with neural induction media, which was fully replaced every other day. On 16 DIV, media was fully replaced with neural induction media containing BMP4 (0.5-15 ng/ml), with full media replacement every other day. 2) Aggregate (SFEBq) method. Human ESC colonies were lifted by 1 mg/ml dispase, plated onto gelatin for 1 hr to remove MEFs, then the supernatant containing hESC colonies was collected. After removing excess media, colonies were incubated with 0.25% trypsin for single cell dissociation, which was stopped by serum-containing media with 10 uM ROCK inhibitor (Y27632, REAGENTS DIRECT). Dissociated cells were plated in U-bottom 96 well plates at 9000 cells/well in SFEBq media with 10 uM ROCK inhibitor. BMP4 (5-15 ng/ml) was added at different time points (21 DIV optimal) for 2 weeks with fresh media changes every three days for CPEC induction. 3) Aggregate-monolayer method. SFEBq aggregates (9000 cells/well) were formed as described above. The SFEBq aggregates were dissociated with TrypLE Express (Invitrogen) at 21 DIV (the point of optimal NEC differentiation) and plated onto PDL-laminin-coated 24 well plates at 300,000-600,000 cells/well with 5-15 ng/ml of BMP4. The SFEBq media was changed every 3 days, with or without fresh BMP4, and the culture was analyzed after 1-2 weeks of BMP4 incubation, with greater CPEC differentiation detected at 2 weeks.

Two human ESC lines (H1 and H9) obtained from the WiCell Research Foundation were used in this process. All other reagents, media, and supplements, including the recombinant BMP4, are commercially-available.

REFERENCES WHICH ARE ALL HEREIN INCORPORATED BY REFERENCE IN THEIR ENTIRETY

1. Emerich D F, Skinner S J M, Borlongan C V, Vasconcellos A V, & Thanos C G (2005) The choroid plexus in the rise, fall and repair of the brain. Bioessays 27(3):262-274.
2. Emerich D F, Skinner S J M, Borlongan C V, & Thanos C G (2005) A role of the choroid plexus in transplantation therapy. Cell Transplantation 14(10):715-725.
3. Chodobski A & Szmydynger-Chodobska J (2001) Choroid plexus: target for polypeptides and site of their synthesis. Microscopy Research and Technique 52(1):65-82.
4. Serot J, BÈnÈ M, Foliguet B, & Faure G (2000) Monocyte-derived IL-10-secreting dendritic cells in choroid plexus epithelium. Journal of Neuroimmunology 105(2):115-119.
5. Serot J, BÈnÈ M, & Faure G (2003) Choroid plexus, aging of the brain, and Alzheimer's disease. Front Biosci 8:s515-521.
6. Sousa J, Cardoso I, Marques F, Saraiva M, & Palha J (2007) Transthyretin and Alzheimer's disease: Where in the brain? Neurobiology of Aging 28(5):713-718.
7. Weller R O (1998) Pathology of cerebrospinal fluid and interstitial fluid of the CNS: significance for Alzheimer disease, prion disorders and multiple sclerosis. Journal of Neuropathology & Experimental Neurology 57(10):885.
8. Herbert J, et al. (1986) Transthyretin: A choroid plexus-specific transport protein in human brain: The 1986 S. Weir Mitchell Award. Neurology 36(7):900.
9. Schwarzman A L, et al. (1994) Transthyretin sequesters amyloid beta protein and prevents amyloid formation. Proceedings of the National Academy of Sciences of the United States of America 91(18):8368.
10. Schwarzman A L, et al. (2004) Amyloidogenic and anti-amyloidogenic properties of recombinant transthyretin variants. Amyloid 11(1):1-10.
11. Costa R, Ferreira-da-Silva F, Saraiva M J, & Cardoso I (2008) Transthyretin protects against A-beta peptide toxicity by proteolytic cleavage of the peptide: a mechanism sensitive to the kunitz protease inhibitor. PLoS One 3(8).
12. Buxbaum J N, et al. (2008) Transthyretin protects Alzheimer's mice from the behavioral and biochemical effects of AÉi toxicity. Proceedings of the National Academy of Sciences 105(7):2681.
13. Choi S, et al. (2007) Accelerated A {beta} Deposition in APPswe/PS1 { Delta} E9 Mice with Hemizygous Deletions of TTR (Transthyretin). Journal of Neuroscience 27(26):7006.
14. Maurizi C P (2010) Choroid plexus portals and a deficiency of melatonin can explain the neuropathology of Alzheimer's disease. Medical hypotheses.
15. Silverberg G D, Mayo M, Saul T, Rubenstein E, & McGuire D (2003) Alzheimer's disease, normal-pressure hydrocephalus, and senescent changes in CSF circulatory physiology: a hypothesis. The Lancet Neurology 2(8):506-511.
16. Skinner S, et al. (2006) Choroid plexus transplants in the treatment of brain diseases. Xenotransplantation 13(4):284-288.
17. Johanson C E, Duncan J A, Stopa E G, & Baird A (2005) Enhanced prospects for drug delivery and brain targeting by the choroid plexus-CSF route. Pharmaceutical research 22(7):1011-1037.
18. Chauhan A N & Lewis P D (1979) A quantitative study of cell proliferation in ependyma and choroid plexus in the postnatal rat brain. Neuropathology and Applied Neurobiology 5(4):303-309.
19. Itokazu Y, et al. (2006) Choroid plexus ependymal cells host neural progenitor cells in the rat. Glia 53(1):32-42.
20. Kaplan M S (1980) Proliferation of epithelial cells in the adult primate choroid plexus. The Anatomical Record 197 (4):495-502.
21. Currie D S, Cheng X, Hsu C, & Monuki E S (2005) Direct and indirect roles of CNS dorsal midline cells in choroid plexus epithelia formation. Development 132(15):3549.
22. Furuta Y, Piston D, & Hogan B (1997) Bone morphogenetic proteins (BMPs) as regulators of dorsal forebrain development. Development 124(11):2203.
23. Fernandes M, Gutin G, Alcorn H, McConnell S K, & Hebert J M (2007) Mutations in the BMP pathway in mice support the existence of two molecular classes of holoprosencephaly. Development 134(21):3789.
24. Hebert J M, Mishina Y, & McConnell S K (2002) BMP signaling is required locally to pattern the dorsal telencephalic midline. Neuron 35(6):1029-1041.
25. Cheng X, et al. (2006) Central roles of the roof plate in telencephalic development and holoprosencephaly. Journal of Neuroscience 26(29):7640.
26. Hu J S, et al. (2008) Border formation in a Bmp gradient reduced to single dissociated cells. Proceedings of the National Academy of Sciences 105(9):3398.
27. Mangale V S, et al. (2008) Lhx2 selector activity specifies cortical identity and suppresses hippocampal organizer fate. Science 319(5861):304.
28. Monuki E S, Porter F D, & Walsh C A (2001) Patterning of the dorsal telencephalon and cerebral cortex by a roof plate-Lhx2 pathway. Neuron 32(4):591-604.
29. Eiraku M, et al. (2008) Self-organized formation of polarized cortical tissues from ESCs and its active manipulation by extrinsic signals. Cell stem cell 3(5):519-532.
30. Elkabetz Y, et al. (2008) Human ES cell-derived neural rosettes reveal a functionally distinct early neural stem cell stage. Genes & development 22(2):152.
31. Watanabe K, et al. (2005) Directed differentiation of telencephalic precursors from embryonic stem cells. Nature neuroscience 8(3):288-296.

32. Anonymous (Allen Mouse Brain Atlas [Internet]. Seattle (Wash.): Allen Institute for Brain Science. ©2009. Available from: http://mouse.brain-map.org.
33. Swetloff A, Greenwood S, Wade A M, & Ferretti P (2006) Growth of choroid plexus epithelium vesicles in vitro depends on secretory activity. Journal of cellular physiology 208(3):549-555.
34. Thomas T & Dziadek M (1993) Capacity to form choroid plexus-like cells in vitro is restricted to specific regions of the mouse neural ectoderm. Development 117(1):253.
35. Zhang S C, Wernig M, Duncan I D, Br stle O, & Thomson J A (2001) In vitro differentiation of transplantable neural precursors from human embryonic stem cells. Nature biotechnology 19(12):1129-1133.
36. Wilson P & Stice S (2006) Development and differentiation of neural rosettes derived from human embryonic stem cells. Stem Cell Reviews and Reports 2(1):67-77.
37. Gage F (2000) Mammalian neural stem cells. Science 287(5457):1433.
38. Reynolds B A & Weiss S (1992) Generation of neurons and astrocytes from isolated cells of the adult mammalian central nervous system. Science 255(5052):1707.
39. Gotz M & Huttner W (2005) The cell biology of neurogenesis. Nature Reviews Molecular Cell Biology 6(10):777-788.
40. Huang X, et al. (2009) Sonic hedgehog signaling regulates a novel epithelial progenitor domain of the hindbrain choroid plexus. Development 136(15):2535.

The invention claimed is:

1. A method of inducing choroid plexus epithelial cells in vitro comprising
deriving neuroepithelial cells from embryonic stem cells; and
deriving choroid plexus epithelial cells from the neuroepithelial cells by adding an effective amount of bone morphogenetic protein BMP4 to the neuroepithelial cells,
wherein the embryonic stem cells are human or mouse cells.

2. The method of claim 1, wherein the embryonic stem cells are human embryonic stem cells.

3. The method of claim 1, wherein the embryonic stem cells are mouse embryonic stem cells.

4. The method of claim 1, wherein the neuroepithelial cells are aggregated.

5. The method of claim 1, wherein the embryonic stem cells are aggregated.

6. The method of claim 5, wherein the aggregated embryonic stem cells are in the form of an embryoid body or an embryoid body-like aggregate.

7. The method of claim 1, wherein the neuroepithelial cells are in the form of single cells.

8. The method of claim 1, wherein the effective amount of the bone morphogenetic protein is between 0.5-50 ng/ml.

9. The method of claim 8, wherein the effective amount of the bone morphogenetic protein is 5 ng/ml.

10. The method of claim 1, wherein the choroid plexus epithelial cells are identified using a combination of genetic markers, antibodies, histology inspection, or functional assays.

11. The method of claim 1, wherein the choroid plexus epithelial cells express one or more of choroid plexus epithelial cell markers selected from the group consisting of Ttr, Msx1, Agp1, Cldn1, Otx2 and Lmx1a.

* * * * *